United States Patent
Tanno

(10) Patent No.: US 6,813,030 B2
(45) Date of Patent: Nov. 2, 2004

(54) OPTICAL INTERFERENCE TOMOGRAPHIC IMAGE OBSERVING APPARATUS

(75) Inventor: Naohiro Tanno, Yamagata (JP)

(73) Assignee: Japan Science and Technology Corporation, Kawaguchi (JP)

( * ) Notice: Subject to any disclaimer, the term of this patent is extended or adjusted under 35 U.S.C. 154(b) by 154 days.

(21) Appl. No.: 10/203,786

(22) PCT Filed: Feb. 14, 2001

(86) PCT No.: PCT/JP01/01007

§ 371 (c)(1),
(2), (4) Date: Aug. 14, 2002

(87) PCT Pub. No.: WO01/61318

PCT Pub. Date: Aug. 23, 2001

(65) Prior Publication Data

US 2003/0011782 A1 Jan. 16, 2003

(30) Foreign Application Priority Data

Feb. 18, 2000 (JP) ........................................ 2000-040883

(51) Int. Cl.[7] ............................. G01B 11/02; G01B 9/02
(52) U.S. Cl. ....................... 356/497; 356/477; 356/479; 356/484; 356/499
(58) Field of Search ................................ 356/497, 477, 356/479, 484, 499

(56) References Cited

U.S. PATENT DOCUMENTS

| | | | | |
|---|---|---|---|---|
| 4,910,404 A | * | 3/1990 | Cho et al. | 250/358.1 |
| 5,320,106 A | * | 6/1994 | Tanaka | 600/466 |
| 5,351,278 A | * | 9/1994 | Koshishiba et al. | 378/22 |
| 6,680,779 B2 | * | 1/2004 | Toida | 356/479 |
| 6,687,010 B1 | * | 2/2004 | Horii et al. | 356/479 |

FOREIGN PATENT DOCUMENTS

| | | |
|---|---|---|
| JP | 56-129826 | 10/1981 |
| JP | 4-142430 | 5/1992 |
| JP | 6-63048 | 3/1994 |
| JP | 6-63049 | 3/1994 |
| JP | 6-70881 | 3/1994 |
| JP | 6-331441 | 12/1994 |
| JP | 9-133582 | 5/1997 |
| JP | 10-281872 | 10/1998 |

OTHER PUBLICATIONS

Author:Naohiro Tanno, Title: "Optical Coherence Fault Image Method & Application of Method to a Biological Image", Publication Date: Dec. 1999 (Sub. to Pub. date Sep. 11, 1998), Kougaku (Japanese Journal of Optics), vol. 28, No. 3, pp. 116–125.

* cited by examiner

*Primary Examiner*—Frank G. Font
*Assistant Examiner*—Khaled Brown
(74) *Attorney, Agent, or Firm*—Oblon, Spivak, McClelland, Maier & Neustadt, P.C.

(57) ABSTRACT

An optical interference tomographic image observing apparatus is provided so as to detect the static or dynamic structure at a deep portion of a living body or the like and provide a multidimensional image thereof for observation.

The optical interference tomographic image observing apparatus includes a rotary prism apparatus which includes a Littrow reflector prism (1) having a 90-degree vertex and disposed near a circumference of a rotary body (4) in such a manner that a surface facing the vertex extends substantially perpendicular to a tangential line of the circumference, the prism having a characteristics such that when a light beam impinges the surface, the light beam is reflected in a direction parallel to the incidence direction. Through utilization of the characteristics, the reflection point can be scanned in a predetermined direction as the rotary body (4) rotates; and a delay reflection light beam is periodically generated when the rotary body rotates in the travel direction of the light beam and a progressive reflection light beam is periodically generated when the rotary body rotates in the opposite direction.

9 Claims, 12 Drawing Sheets

OPTICAL INTERFERENCE TOMOGRAPHIC IMAGE OBSERVING APPARATUS

TECHNICAL FIELD

The present invention relates to a technique for detecting back-scattering light from a scattering potential which has a scattering center at a micro object or the like located within, for example, a living body, which is a medium that strongly scatters light; obtaining information regarding a scattering position and information regarding reflection amplitude by use of interference measurement means which utilizes a phenomenon that coherence is present even in reflection light from an object that strongly scatters light and which utilizes the shortness of coherence length of low-coherence light; and obtaining single-dimensional or two-dimensional image data, or multidimensional image data such as three-dimensional image data, while scanning the interior of the object. More particularly, the present invention relates to an optical interference tomographic image observing apparatus which enables easy observation of a tomographic image of a light-scattering medium such as a living body by use of a remote device.

BACKGROUND ART

An attempt for obtaining a reflection tomographic image of a living body, which is a medium that strongly scatters light, starts from construction of an interferometer by use of low-coherence light (see Naohiro Tanno, "*Kogaku*" Vol. 28, No. 3, pp. 116–125 (1999)). A conventional technique will be described with reference to FIGS. 1 and 2.

FIG. 1 is a diagram showing the structure of a conventional light-wave reflection image measurement apparatus proposed by the present inventors.

In this light-wave reflection image measurement apparatus, a light beam from a low-coherence (also referred to as partial-coherence) light source 71 is introduced directly to a Michelson's interferometer in order to split the beam into two beams by means of a beam splitter 73. One of the split beams, which is to be used as reference light, undergoes frequency shift. The frequency-shifted light beam is reflected by a movable reflection mirror 72, which also serves to change a depth position within an object, and is caused to enter a photo detector 75. The other light beam or transmission light is supplied to an object 74 to be measured as object irradiation light. The light is scatter-reflected by a layer of scattering objects located at a deep portion of the object 74 and having a different refraction index. The reflection light, serving as object reflection light, is mixed with the reference light by means of the beam splitter 73 so as to cause interference. As a result, a beat signal is detected by means of the photo detector 75. While the positional relation between the illumination light and the object is changed in order to effect scanning, the detected electric signals are fed to a computer via a filter and an amplification/signal processing section, whereby the detected electric signals are stored in the computer. The thus-stored electric signals are converted to image data in order to obtain a reflection tomographic image.

FIG. 2 is a diagram showing the structure of a conventional tomographic-image observation apparatus which employs a structure on the basis of the above-described principle and in which optical fibers are disposed to form optical paths in order to cope with vibration and facilitate handling (see, for example, Japanese *Kohyo* (PCT) Patent Publication No. 6-511312).

As shown in FIG. 2, a light beam from a light source 81 propagates through a fiber 82 and enters a splitter/mixer circuit 86. One light beam emitted from the splitter/mixer circuit 86 propagates through a fiber. Light coming out from the outgoing end of the fiber is converged by means of a convex lens 83. As a result, the light is reflected by an object 84, and the reflection light serves as object reflection light. After impartment of a frequency shift by means of a piezo-oscillation phase shifter 85, the other light beam emitted from the splitter/mixer circuit 86 is reflected by a movable reflection mirror 80, and the reflection light serves as reference light, which is mixed and is caused to interfere with the object reflection light by means of the splitter/mixer circuit 86. The mixed light enters a photo detector 87, whereby a reflection tomographic image can be observed in the same manner as described above.

Conventional interference measurement methods all utilize a movable reflection mirror for changing light reflection position (reference reflection position). In general, the movable reflection mirror is a reflection mirror attached to a linear actuator or a galvano-motor. Since the linear actuator moves an object back and forth via gears, the moving speed is as low as several mm/sec. In another method, a long fiber is wound around an electrostrictive element such as an element made of PZT, and the length of a reflection light path is changed through extension and contraction of the fiber.

DISCLOSURE OF THE INVENTION

Among the above-described conventional methods, the method employing a reflection mirror attached to a linear actuator or the like involves problems in that high-speed sweeping is difficult, and that when the mirror is moved back and forth periodically, linearity is deteriorated due to backlash and other causes.

Meanwhile, the method in which a long fiber is wound around an electrostrictive element such as an element made of PZT and the length of a reflection light path is changed through extension and contraction of the fiber involves a problem in that since a path for reference light becomes excessively long, the temperature varies, and the length of a path for object light must be increased.

Furthermore, the apparatus utilizing a linear actuator and the apparatus utilizing an electrostrictive element are both large in size, and fabrication of a compact, transportable apparatus including an interferometer is difficult.

Moreover, when sweeping speed is low, a very long time is needed to complete tomographic image measurement, which makes applying the tomographic image measurement to examination of a living body or a moving object difficult. In addition, when the path for reference light and the path for reflection light are made excessively long, optical signals attenuate excessively. In this case, the SN ratio of an obtained image decreases, which makes observation of a deep portion of an object difficult.

In order to solve the above-described problems, the present invention proposes a method and a specific apparatus which utilizes a rotating Littrow reflector prism and which can reflect a light beam in order to produce a delay reflection light beam or a progressive reflection light beam which travels toward the incoming direction of the light beam, even when the reflection point moves along a circumference of a rotary body upon rotation thereof or a surface of the prism facing the vertex thereof inclines. The method and the apparatus utilize the features of the prism such that the prism reflects a light beam toward the direction from which the light beam comes, and even when the incoming light beam inclines with respect to the surface facing the 90-degree vertex, the prism accurately reflects a light beam toward the incoming direction. Further, the present invention realizes a reliable, high-speed-scanning reflection mirror by attaching prisms on a small, high-speed motor, and opens to the road to a compact, simplified, transportable apparatus which can be used practically for optical interference tomographic image observation, which is an object of the present invention. Moreover, another object of the present invention is to provide an optical interference tomographic image observing apparatus which extracts reflection signals of wide dynamic range and high SN ratio through high-speed scanning in order to detect a static or dynamic structure of a deep portion of, for example, a living body and to produce a multidimensional image for observation.

In order to achieve the above objects, the present invention provides the following.

[1] An optical interference tomographic image observing apparatus, characterized by comprising a rotary prism apparatus which includes a Littrow reflector prism having a 90-degree vertex and disposed near a circumference of a rotary body in such a manner that a surface facing the vertex extends substantially perpendicular to a tangential line of the circumference, the prism having a characteristics such that when a light beam impinges the surface, the light beam is reflected in a direction parallel to the incidence direction, wherein through utilization of the characteristics, the reflection point can be scanned in a predetermined direction as the rotary body rotates; and a delay reflection light beam is periodically generated when the rotary body rotates in the travel direction of the light beam and a progressive reflection light beam is periodically generated when the rotary body rotates in the opposite direction.

[2] An optical interference tomographic image observing apparatus as described in [1] above, further comprising:

means for splitting a light beam from a low-coherence light source into two light beams, one of the light beams, serving as reference light, being delayed or advanced by means of rotary scanning of the reflection point in order to obtain a reflection light beam having a Doppler shift frequency, and the other light beam being converged to an object to be measured which has a multilayer structure in terms of refraction index distribution; an objective lens for capturing object reflection light from a scattering potential portion at a deep portion of the multilayer object; a photo detector for performing heterodyne detection for obtaining a beat signal of the shift frequency, which is generated on the basis of the low coherence, characterized in that a maximum interference signal can be obtained only when the reference light and the object reflection light merge together after passage through respective optical paths having the same optical path length as measured from the split point; means for calculating, in the form of coordinates, the scanned reflection point of the delay or progressive reflection light beam; and a signal control processing system, a computer, and a display which measure and display a reflection tomographic image, while using, as image data, the coordinates and an amplitude of the beat signal representing reflection light from the scattering potential at the deep portion of the object to be measured.

[3] An optical interference tomographic image observing apparatus as described in [2] above, wherein the means for calculating, in the form of coordinates, the scanned reflection point of the reflection light beam includes a photo detector for capturing deflection angle reflection light from the rotary prism, wherein the photo detector generates a timing pulse upon detection of the deflection angle reflection light before generation of the reflection light beam; and the scanned reflection point is calculated from the rotation frequency, rotation circumferential length, and rotation angle of the rotary prism, and is used as a coordinate of the scattering potential.

[4] An optical interference tomographic image observing apparatus as described in [2] above, wherein the travel direction of the light beam emitted from the low-coherence light source is referred to as a Z axis; a semi-transparent reflection mirror is provided as the means for splitting the light beam into two beams; the objective lens is disposed in a direction toward which a light beam passing through the semi-transparent reflection mirror travels, the light beam serving as object irradiation light; a direction along which a reflection light beam from the semi-transparent reflection mirror serving as reference light travels is referred to as a Y axis; the light source, the semi-transparent reflection mirror, and the objective lens are integrated into a unit structure; and a mechanism for rotating the unit structure about the Y axis is provided in order to rotate the unit structure to thereby sweep the irradiation point on the object to be measured along the X-axis direction, whereby observation of a two-dimensional tomographic image on an X-Z plane is enabled.

[5] An optical interference tomographic image observing apparatus as described in [2] above, wherein the respective means are accommodated within a casing; a dielectric multilayer film reflection mirror which reflects only the wavelength band of the low-coherence light source is disposed before the photo detector in order to reflect and guide the mixed-wave interference wave to the photo detector; a light source whose wavelength band differs from that of the low-coherence light source is provided; a second half mirror is provided in order to reflect light emitted from the second light source and cause the light to pass through the dielectric multilayer film reflection mirror, the half mirror, and the objective lens in order to radiate the object to be measured, reflection light from the surface of the object traveling back along the above-described optical path, and passing through the second half mirror; a CCD camera is provided in the same casing in order to capture the image of the surface having magnified by the objective lens; and a display is disposed outside the casing in order to enable previous observation of a measurement position on the object.

[6] An optical interference tomographic image observing apparatus as described in [5] above, wherein the casing is equipped with a grip handle which has a switch for starting acquisition of measurement data of the tomographic image after positioning of the measurement point through observation of the measurement point.

[7] An optical interference tomographic image observing apparatus as described in [4] above, further comprising a rotation mechanism which rotates about the X axis and which receives the casing on which the unit structure is disposed at an angle of 90 degrees, whereby, in addition to the observation of a two-dimensional tomographic image on an X-Z plane, scanning along the Y-axis direction is effected by the rotation mechanism in order to enable observation of a three-dimensional tomographic image.

[8] An optical interference tomographic image observing apparatus as described in [7] above, wherein the objective lens is replaced with an objective lens for funduscopy; and the object irradiation light is scanned by use of a galvanomirror.

[9] An optical interference tomographic image observing apparatus as described in any one of [1] to [7] above, wherein the optical path for reference light is turned up and down by a group of reflection mirrors in order to increase the length of the optical path; and an optical fiber having a length corresponding to the increased length is disposed in the optical path extending between the half mirror for splitting and the object, whereby remote measurement is enabled.

[10] An optical interference tomographic image observing apparatus as described in any one of [1] to [7] above, wherein an optical fiber is disposed in the optical path for reference light in order to increase the length of the optical path; and an optical fiber capable of transmitting images and having a length corresponding to the increased length is disposed in the optical path extending between the half mirror for splitting and the object, whereby remote measurement is enabled.

BEST MODE FOR CARRYING OUT THE INVENTION

Embodiments of the present invention will now be described in detail.

Figure 1:
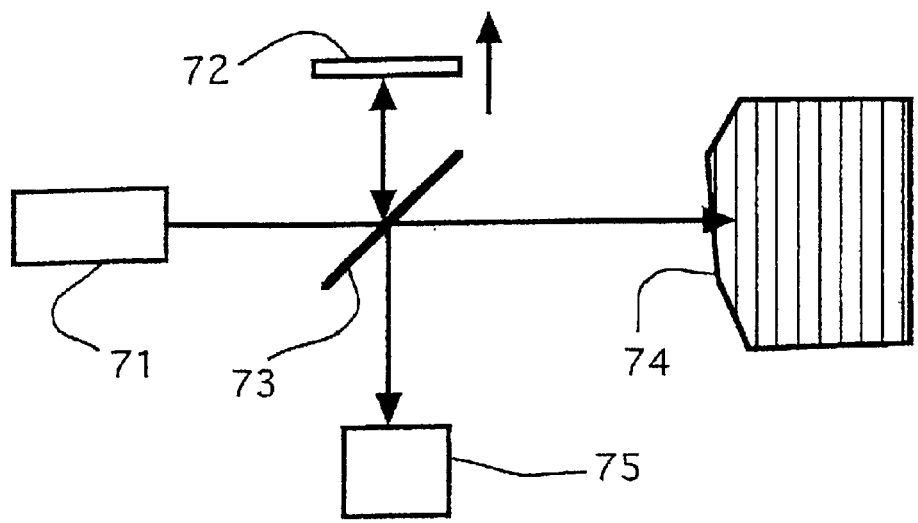
FIG. 1 is a structural diagram of a conventional lightwave reflection image measurement apparatus configured by use of a movable reflection mirror.
Figure 2:
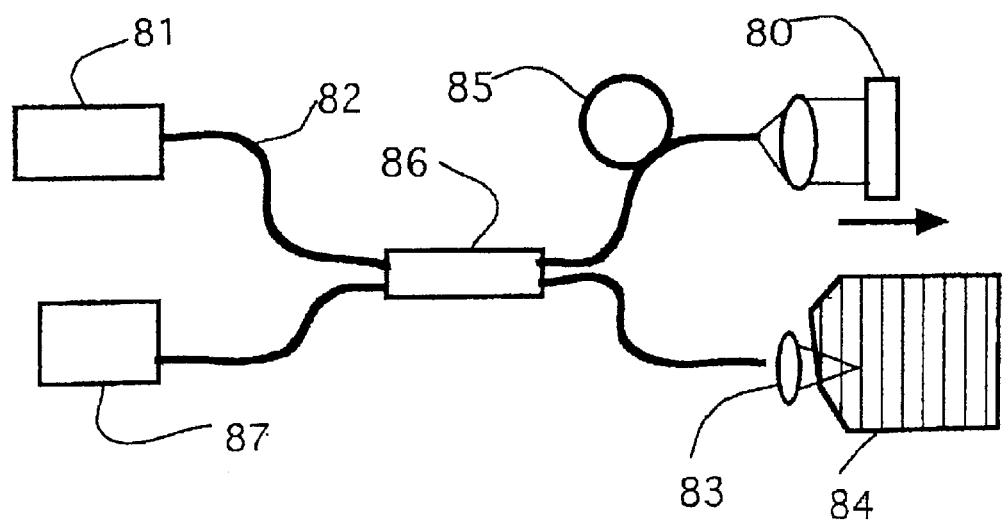
FIG. 2 is a structural diagram of a conventional tomographic-image observation apparatus configured by use of optical fibers and a movable reflection mirror.
Figure 3:
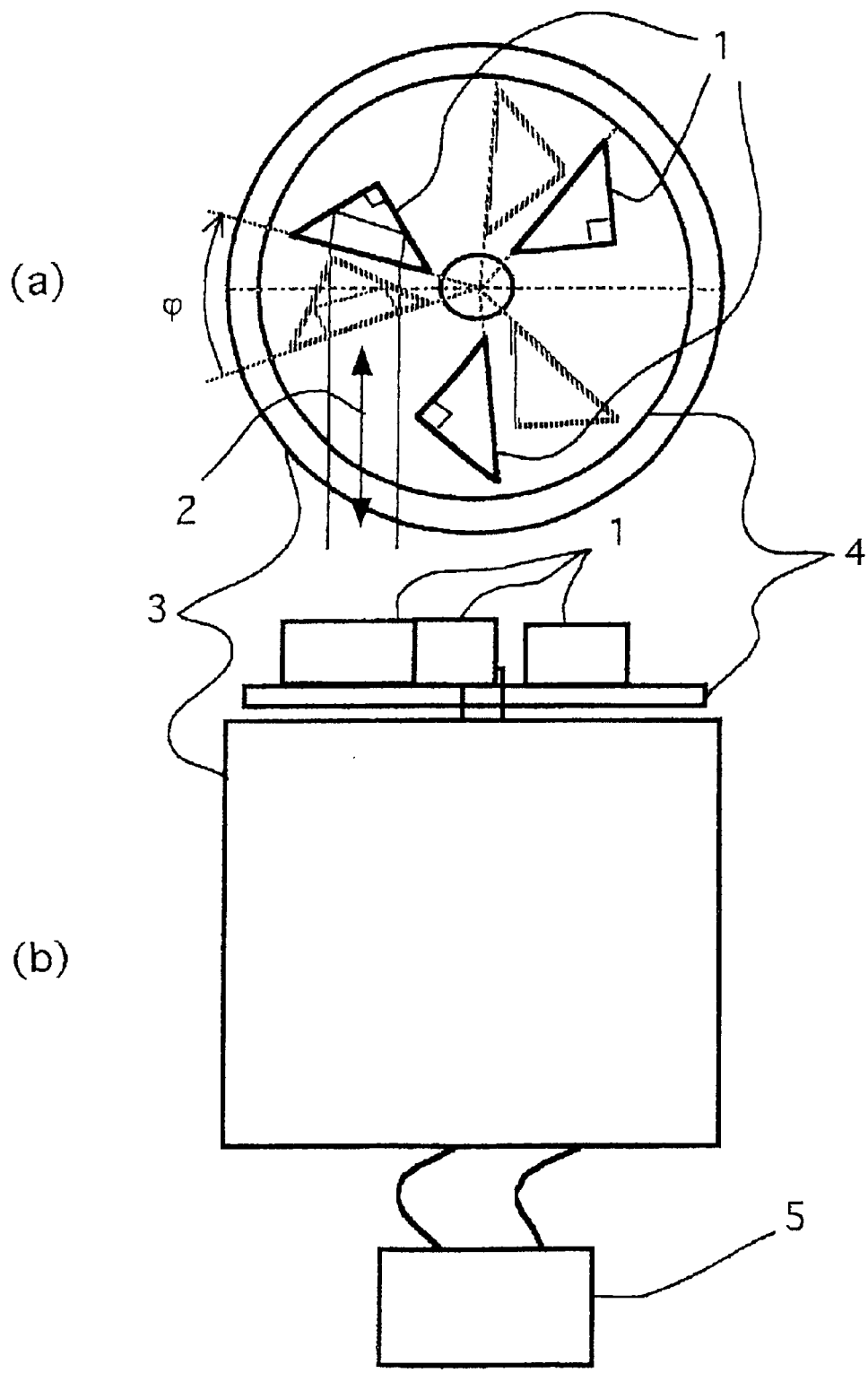
FIG. 3 is a structural diagram of a reflection-point scanning rotary prism apparatus according to an embodiment of the present invention.
Figure 4:
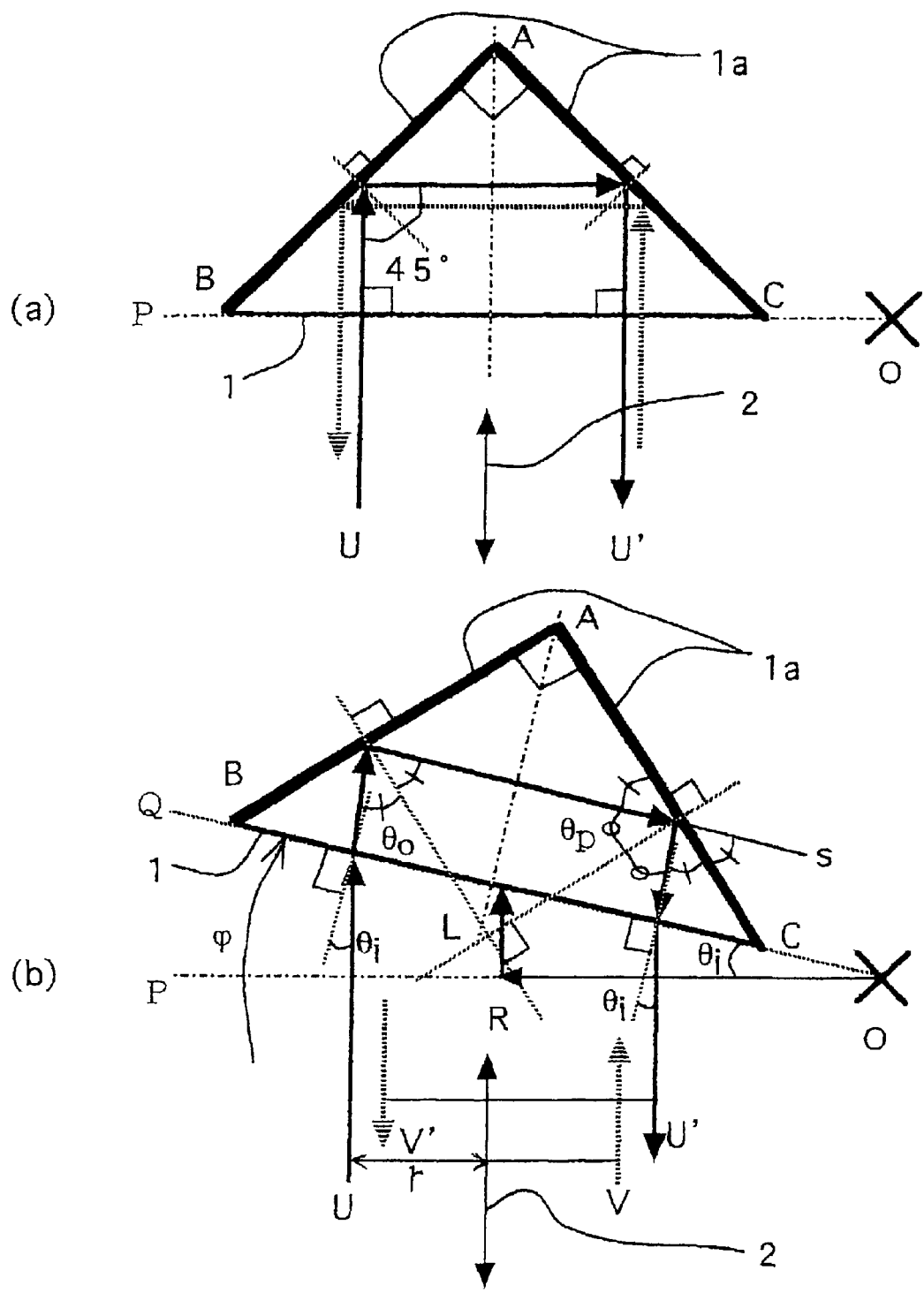
FIG. 4 is a diagram to be used for explaining light reflection characteristics of a 45-degree right-angle prism of the reflection-point scanning rotary prism apparatus according to the embodiment of the present invention.

FIG. 3 is a structural diagram of a reflection-point scanning rotary prism apparatus according to an embodiment of the present invention, wherein FIG. 3(a) is a top view of the apparatus, and FIG. 3(b) is a side view of the apparatus. FIG. 4 is a diagram to be used for explaining light reflection characteristics of a 45-degree right-angle prism of the reflection-point scanning rotary prism apparatus, wherein FIG. 4(a) is an explanatory view showing reflection light in the case in which an incoming beam enters a diagonal surface perpendicularly thereto, and FIG. 4(b) is an explanatory view showing reflection light in the case in which an incoming beam enters the diagonal surface not perpendicularly thereto, due to rotation of the prism.

As shown in these drawings, an incident light beam 2 from a low-coherence light source is caused to enter a rotary prism 1. As shown in FIG. 4, the rotary prism 1 is a Littrow reflector prism whose one vertex angle is 90 degrees and in which a reflection thin film 1a of a metal, such as aluminum, which reflects light is vapor-deposited on the sides forming the 90-degree vertex. As shown in FIG. 3, in consideration of load balance, two or three prisms 1 are disposed on and fixed to a rotary plate 4, serving as a rotary body, symmetrically with respect to the axis of rotation. The rotary plate 4 is rotated by power of a motor 3. FIG. 3 shows an example in which the rotary plate 4 rotates in the direction indicated by $\phi$.

First, light reflection characteristics of the Littrow reflector prism will be described with reference to FIG. 4.

When a light beam U enters a diagonal surface BC perpendicularly thereto, as shown in FIG. 4(a), 45-degree incidence/reflection is repeated at two sides (AB, AC) of the prism, and thereby producing a reflection light beam U', which travels toward the direction from which the light beam U comes. The position of the light beam U is determined in such a manner that its cross section becomes symmetric with respect to a center line of the vertex. In this case, a left-hand half of the light beam is reflected to the right side, and a right-hand half of the light beam is reflected to the left side. Therefore, the light beam is reflected toward the incidence direction in such a manner that its entire wave front becomes parallel to the diagonal surface.

Next, there will be considered a case in which the prism 1 has been rotated by a rotation angle θi about the rotational axis O. In this case, internal reflection as shown in FIG. 4(b) occurs. Specifically, the light beam U enters the diagonal surface BC at an angle θi. When the refraction index of the prism glass is represented by n, the incident angle $\theta_o$ to the side AB is represented by 45°−θr, where θr is determined by $\sin^{-1}(\sin\theta i/n)$ in accordance with Snell's law. Since the reflection light beam traveling from the side AC forms the same angle with respect to a line s shown in FIG. 4(b) as that formed by the incident light beam traveling to the side AB, the reflection light beam U' becomes parallel to the incident light beam U in accordance with Snell's law. At this time, the reflection light beam is shifted to the right, depending on the rotation angle and the radius r of the light beam. In the present invention, the radius of the light beam is set to 6 mm, and the reflection point scanning distance L is as small as about ±1 mm. Therefore, when the turning radius OR is set to 7.5 mm, the rotation angle θi becomes about ±7.6 degrees. In this case, the amount of shift of the axis of reflection light becomes about 10%. Since the amount of shift is sufficiently small as compared to the diameter of the incident light beam, such a shift does not raise any problem in optical interference detection of the present invention. Various types of Littrow reflector prisms are available; e.g., a 45-degree right-angle prism which has only two surfaces forming a 90-degree vertex, a cube corner prism which has six such surfaces, and a prism which has a conical surface. The latter two prisms can reflect a light beam to a direction from which the light beam comes, regardless of whether the light beam approaches the prism from the upper side, the lower side, the left side, or the right side. The prism of the present embodiment provides satisfactory delayed reflection light only when the entire cross section of the light beam is located within the diagonal surface BC of the prism. When the length of the side BC is 10 mm, this requirement is satisfied sufficiently within the above-described rotational angle. As shown in the present embodiment, when the rotational angle is set to 15.2 degrees, a desired reflection-point scanning distance of 2 mm can be attained.

The present invention requires repeated scanning. When the rotational speed of the motor is set to, for example, 6,000 rpm, reflection light can be obtained at a frequency of 300 Hz through reflection by the three prisms shown in FIG. 3, and thus, delay reflection light can be generated at high frequency. The rotational speed of 6,000 rpm can be realized with ease by use of a commercially available small motor. Apparently, progressive reflection light can be generated when the prism apparatus is rotated in a direction opposite that shown in FIG. 3. The prism apparatus can generate delay (progressive) reflection light at an arbitrary period through adjustment of the voltage of a motor power supply 5.

Figure 5:
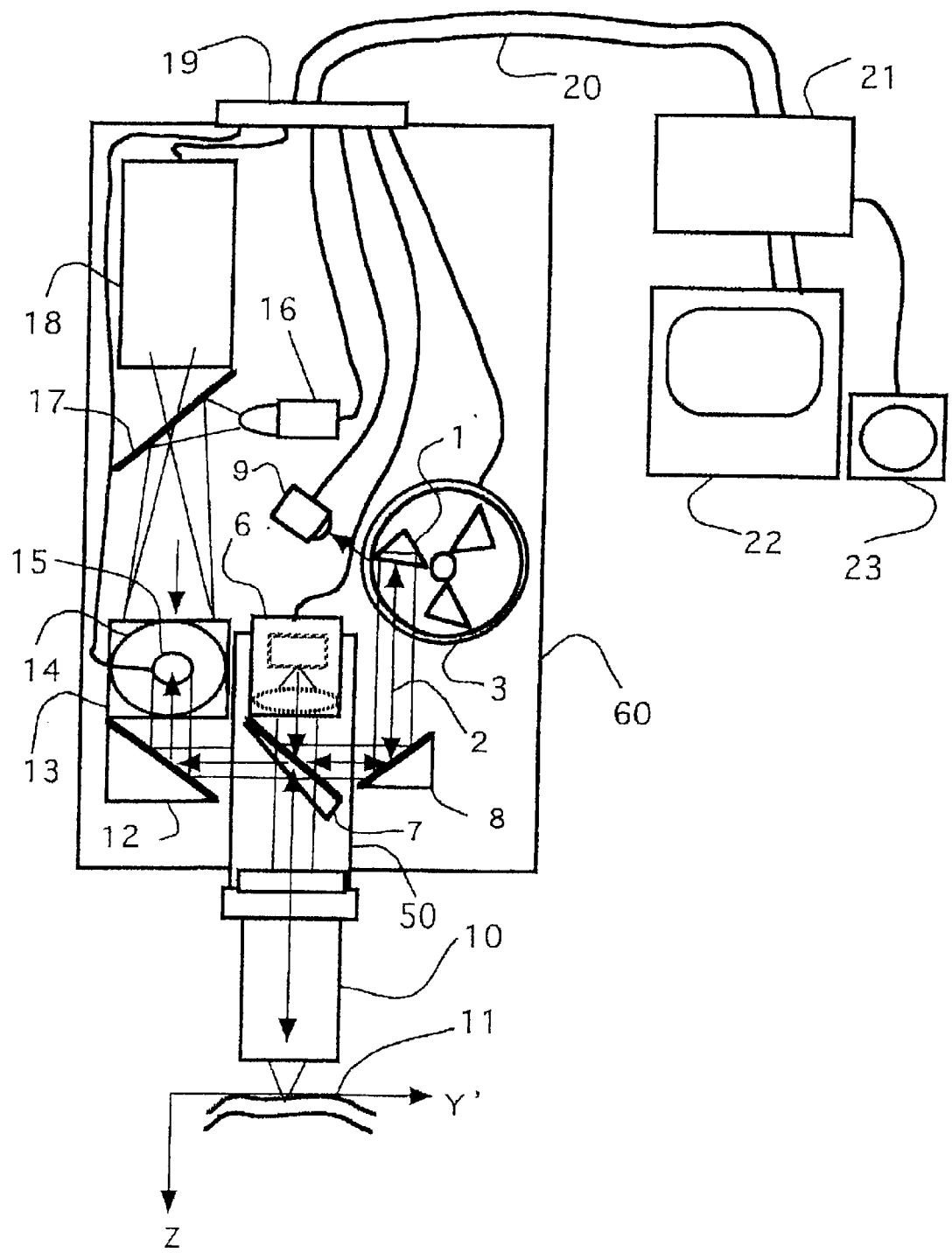
FIG. 5 is a view showing an embodiment of an optical interference tomographic image observing apparatus which includes the reflection-point scanning rotary prism apparatus according to the present invention.

FIG. 5 is a view showing an embodiment of an optical interference tomographic image observing apparatus which includes the above-described rotary prism apparatus.

As shown in FIG. 5, a low-coherence light source 6 is constituted by a light-emitting diode and a convex lens and emits substantially parallel light rays. The light source has a center wavelength λ of 0.88 μm and a wavelength width Δλ of 40 nm and is estimated to have a spatial resolution ΔZ of 8.5 μm, as determined on the basis of the coherence length. The emitted light beam is split into two beams by means of a half mirror 7. One light beam is reflected by means of a reflection mirror 8 and enters the rotary prism 1 of the above-described embodiment. Thus, the light beam is converted to delay reflection light 2 at a predetermined position. The delay reflection light 2 travels back to the half mirror 7 as reference light.

The reflection light from the high speed rotary prism 1 has a Doppler shift frequency fb. For example, in the case of the above-described embodiment, fb=10.6 MHz, as determined from the rotational angular speed of a circumferential point. Meanwhile, the other light beam or transmission light passes through an objective lens 10 and reaches an object 11 to be measured, which has a multi-layer structure, such as a living body. Object reflection light from a deep portion of the object is collected by the objective lens 10 and is caused to travel to the reflection mirror 8, at which the object reflection light is mixed with the reference light so as to produce mixed-wave interference light. The mixed-wave interference light is reflected by means of a reference mirror 12 and is then reflected by means of a dielectric multi-layer film reflection mirror 13 capable of selectively reflecting light having a wavelength of 0.88 μm (wavelength width: 40 nm) such that the reflection light propagates along a direction perpendicular to the sheet of FIG. 5. The reflection light is converged by means of a convex lens 14 and is detected by a photo detector 15. When the electric field of the reference light is represented by Er and the electric field of the object reflection light is represented by Es(x, y, z), due to the square-law detection action involved in photoelectric conversion, the photo detector 15 outputs a signal represented by the following expression, including a heterodyne beat signal.

$$I(x, y, z) = \frac{1}{2\pi \Delta f} \int_{-\infty}^{\infty} G(f)|E_r + E_s(x, y, z)|^2 \, df$$

$$= [DCterms] +$$

$$E_r E_s(x, y, z) \sqrt{\frac{\pi}{\ln 2}} \cos(2\pi f_b t) \exp\left\{-\frac{\pi^2}{\ln 2}[\Delta f(\tau - z/c)]^2\right\}$$

Here, Δf represents a frequency width of the light source; and G(f) represents its frequency distribution function, wherein the frequency is assumed to follow a Gaussian distribution. [DCterms] represents the DC component serving as background noise. τ=(dr−ds)/c, where dr represents the optical distance between the half mirror 7 and the reflection position of the rotary prism 1, ds represents an optical distance to a reflection point on the surface of the object, and z represents the distance between the surface of the object and a reflection position at a deep portion. Accordingly, τ represents a delay time produced by the rotary prism 1 when the surface of the object used as a reference. From Expression (1), it is understood that a sine wave of the beat frequency fb is modulated by a Gaussian function, and that the position of a peak of the modulated wave represents a Z-axis coordinate of a deep portion of the object that reflects light, and the amplitude of the peak represents the scattering intensity of a scattering potential at a reflection point. Reference numeral 19 denotes a wiring terminal; 20 denotes wiring; and 60 denotes a casing.

Figure 6:
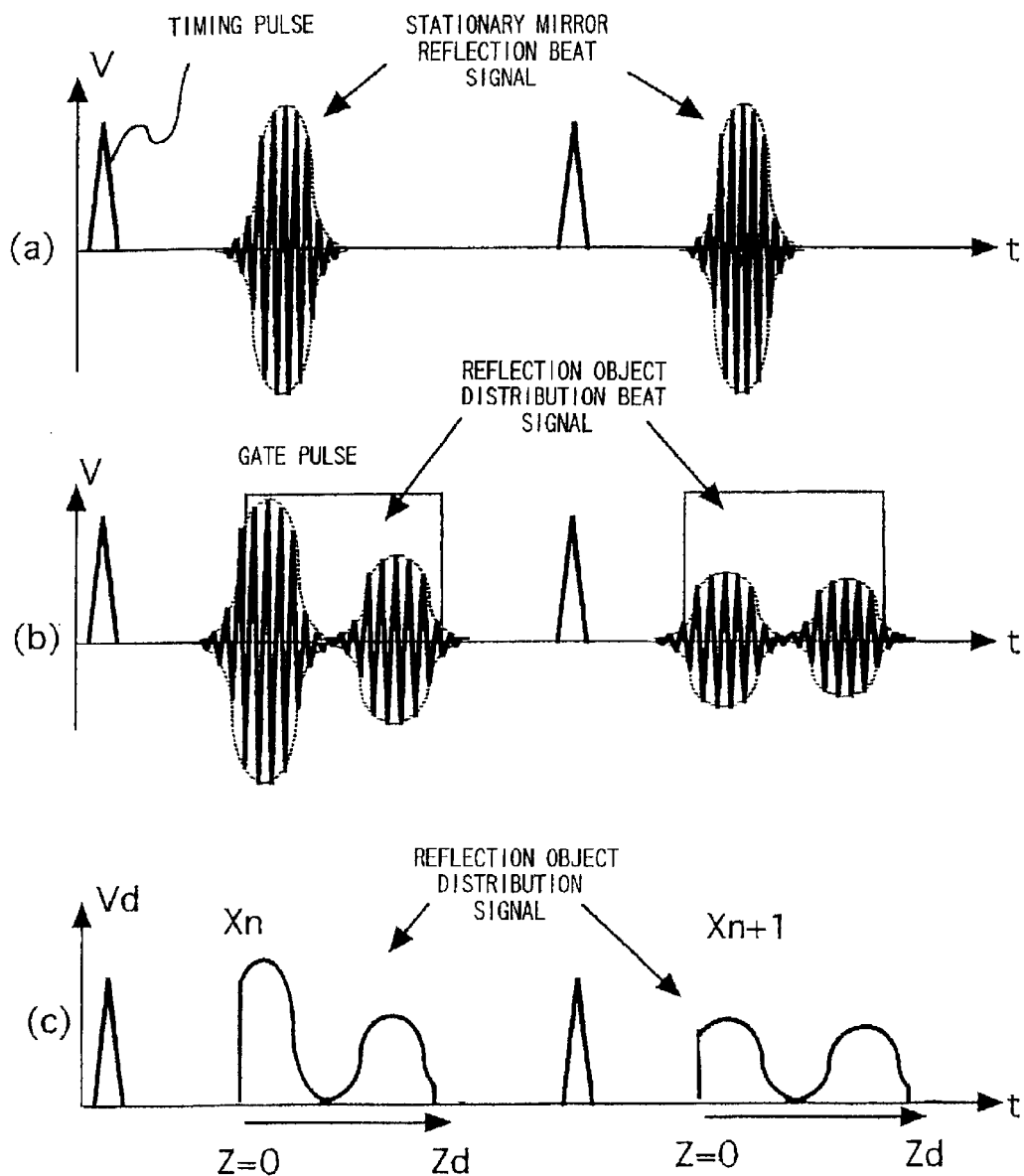
FIG. 6 is a set of graphs showing waveforms of mixed wave interference signals.

FIG. 6 is a set of graphs showing waveforms of mixed-wave interference signals in relation to the present invention, wherein FIG. 6(a) shows timing pulses and a waveform of a beat signal in the case of a stationary mirror, FIG. 6(b) shows a waveform of a beat signal showing a distribution of reflective objects in a deep layer of an object to be measured and setting of gate pulses for determining measurement points, and FIG. 6(c) shows an image signal which is obtained through beat-frequency filtering and representing the distribution of the reflective objects.

FIG. 6(a) shows timing pulses output from a photo diode 9 shown in FIG. 5 and a Doppler beat signal observed when a stationary mirror is placed in place of the object. The timing pulses can be obtained by capturing reflection light from, for example, the metal reflection thin film 1a of the side AB of the rotary prism, before the rotary prism receives the light beam. The time between the pulses corresponding to the distance between the rotary prism. From this, the relative position of the stationary mirror can be calculated. Due to low-coherent time c/Δf (c: velocity of light) shown in Expression (1), the beat signal assumes a pulse shape, which provides a resolution ΔZ in relation to the Z-axis distance of the deep portion of the object. Within an object having a refraction index n, the resolution is represented by ΔZ/n. In a living body or the like, the resolution becomes about 6.5 μm. When the object has a multi-layer structure, a reflection signal as shown in FIG. 6(b) is observed. The incident light beam 2 is received by the rotary prism 1 over a limited period of time. Therefore, a surface position of the object is identified and a gate pulse is generated on the basis of the surface position, and only the beat frequency is filtered. As a result, the waveform shown in FIG. 6(c) is obtained. When the position of the irradiation point on the object 11 to be measured is scanned for each rotary prism, a signal can be obtained each of successive positions Xn, Xn+1, etc., along the X-axis. A pixel signal is produced for each combination of an Z-axis section having a length corresponding to the distance of resolution and an X-axis section having a length corresponding to the diameter of the focal point of the objective lens; e.g., 20 μm, and is then subjected to image processing. A computer 22 performs control of the rotational speed of the prism, storage of data, and necessary computation processing via a control system 21. By virtue of these operations, the computer 22 can immediately display a two-dimensional tomographic image on a display during observation thereof.

The present embodiment includes means for enabling a user to microscopically observe the surface of the object 11 via the objective lens 10. Specifically, as shown in FIG. 5, a high-intensity light emitting diode 16 is disposed at a predetermined position; and the light emitted from the diode 16 is reflected by means of a half mirror 17 as shown in the drawing and is passed through the above-described dielectric multi-layer film reflection mirror 13. At this time, the wavelength range of the light emitting diode 16 is selected so as to fall within a visible range. This visible light is reflected by means of the half mirror 7 so as to illuminate the surface of the object. As a result, reflection light travels backward, passes through the half mirror 17, and reaches a CCD camera 18. For example, when the objective lens 10 has a focal distance f of 16 mm and the CCD camera 18 is equipped with a close-up lens, a microscopic image magnified some tens of times can be obtained. This magnified image is observed by use of a compact liquid-crystal display unit 23 or the like disposed separately. Since light emitted from the low-coherence light source 6 contains a slight amount of a red component, an irradiation point at which a tomographic image is to be observed is also observed within a field of view of the microscope. This method facilitates positioning within the field of view.

Figure 7:
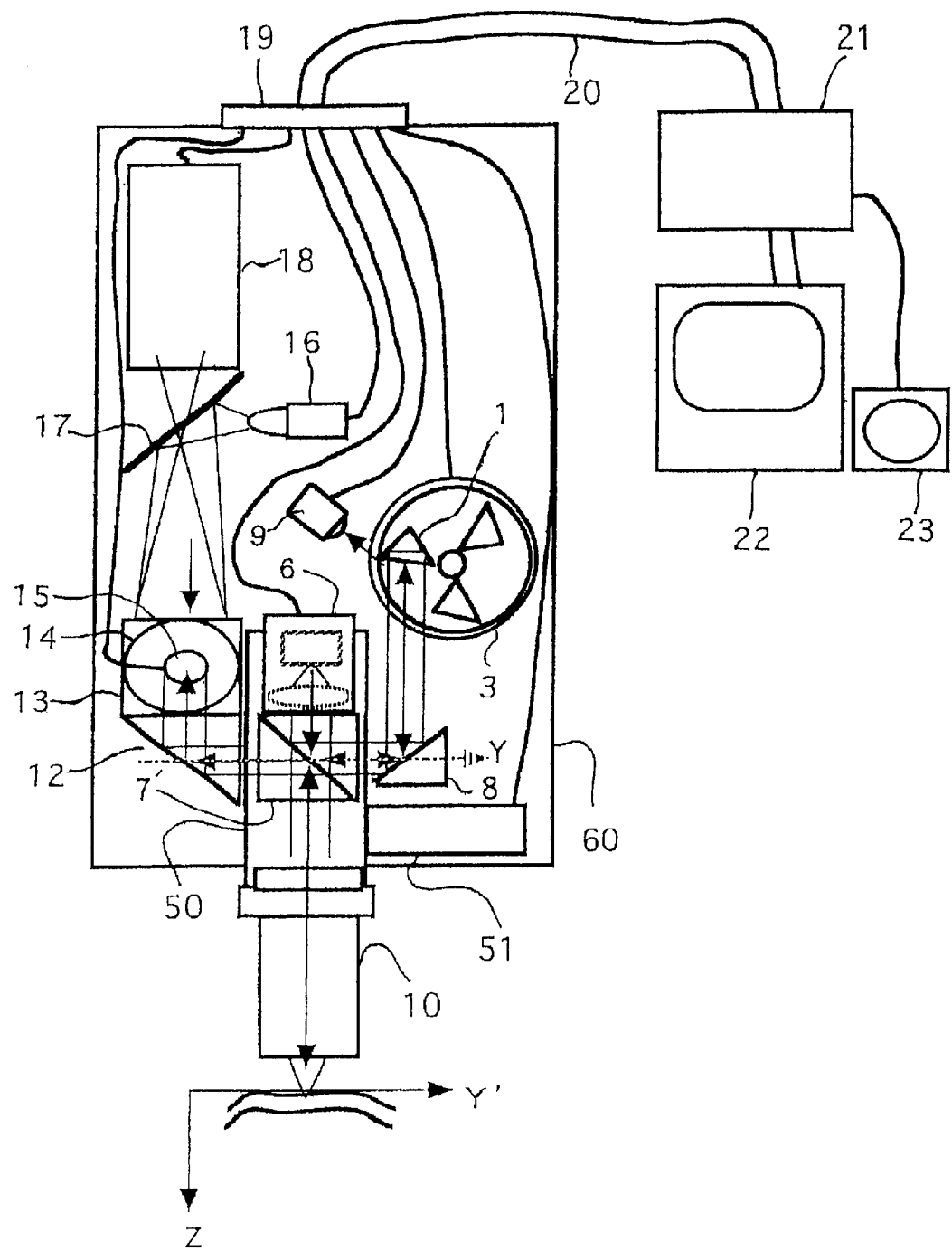
FIG. 7 is a view showing another embodiment of the present invention which is equipped with a mechanism for scanning along an X-axis direction of an object to be measured.

Next, FIG. 7 shows another embodiment which is equipped with a mechanism for scanning along the X-axis direction.

Figure 8:
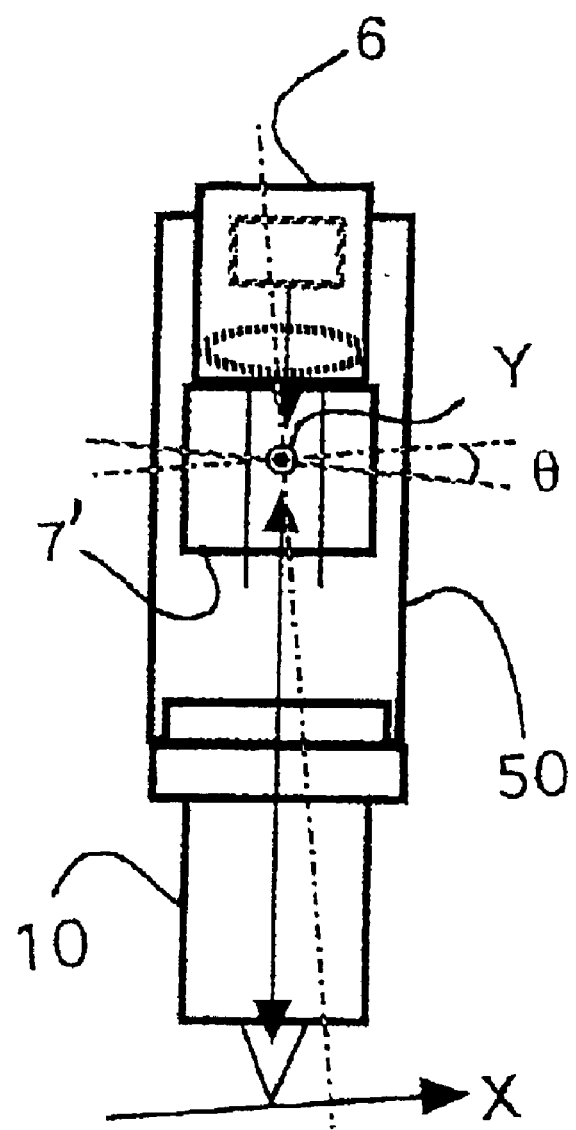
FIG. 8 is a view showing another embodiment of the present invention in which a low-coherence light source, a half mirror, and an objective lens are connected to form a single unit.

As shown in FIG. 7, a low-coherence light source 6, a half mirror 7' (a cube half mirror in this example), and an objective lens 10 are arranged along a straight line and are connected together to form a unit structure 50. As shown in FIG. 7, the direction along which a reflection light beam and a mixed-wave interference light beam travel is referred to as a Y axis. The unit structure 50 is provided with a deflection angle turning mechanism 51, which rotates the unit structure 50 about the Y axis over an angle θ=±4.5 degrees. As a result, when the distance between the Y axis and the object is set to, for example, about 40 mm, as shown in FIG. 8, the irradiation point on the surface of the object can be changed along the X-axis direction by about ±3.0 mm. In an example case in which the X-axis is divided into 300 sections in consideration that the objective lens has a spatial resolution of 20 μm as measured on the irradiation surface, the 300 sections are scanned over one second when the rotary prism generates delay light at 300 Hz. As a result, a two-dimensional tomographic image can be converted to image data within 1 second. In this case, since the irradiation surface becomes arcuate, a correction surface is calculated in advance before obtaining imaged data during subsequent image processing.

Figure 9:
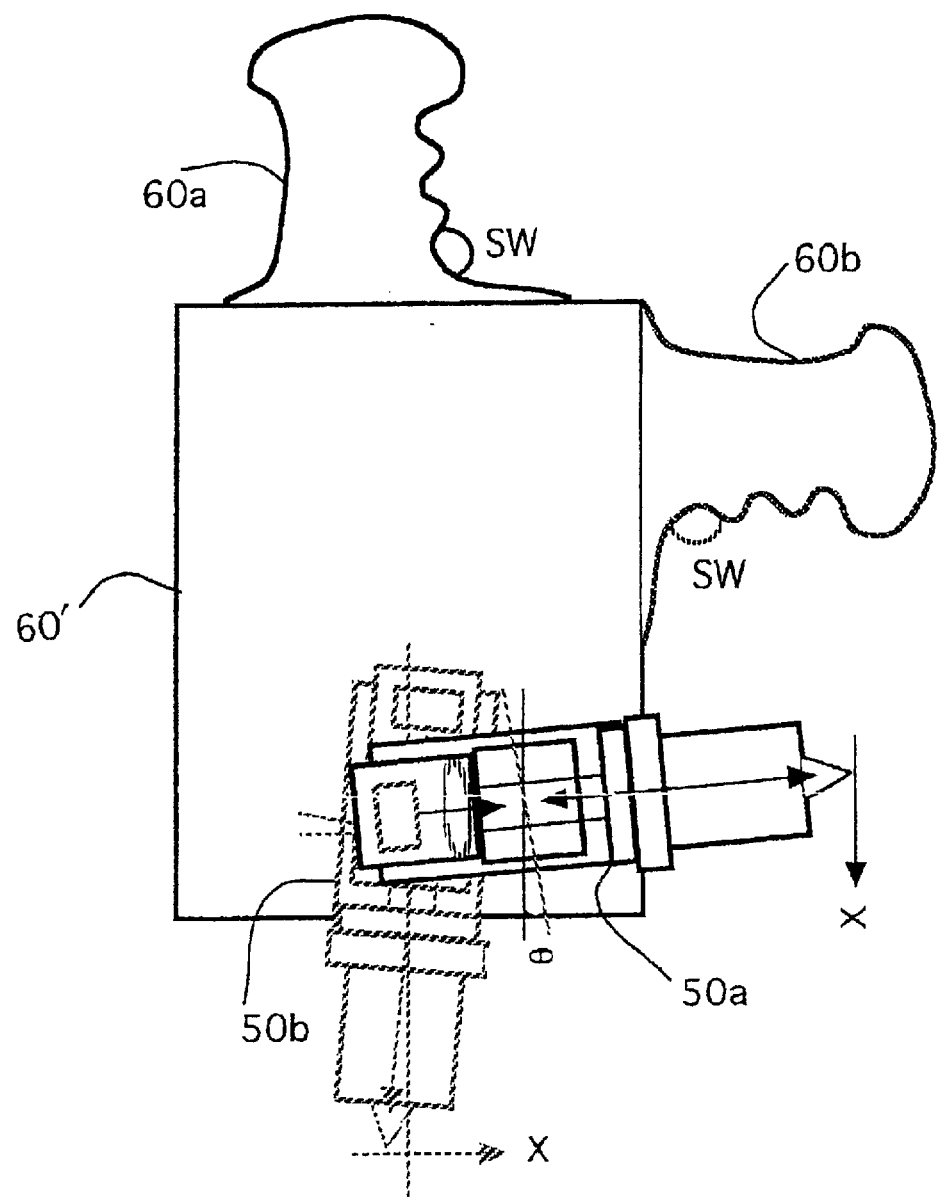
FIG. 9 is a view showing an embodiment of a compact, portable, simplified apparatus according to the present invention.

Next, FIG. 9 shows an embodiment of a compact, portable, simplified apparatus.

In the present embodiment, the control processing system 21, the computer 22, and the compact liquid-crystal display 23 shown in FIG. 5 are disposed outside a casing 60'; and the above-described various components are accommodated in the casing 60' so as to constitute an observation head as shown in FIG. 9. The casing 60' is equipped with a handle 60a for transport, and a switch SW for starting and stopping data acquisition after determination of a measurement point. Thus, the observation head is made transportable. In this case, unlike the case of FIG. 7, the above-described unit structure 50a is rotated by 90 degrees in order to facilitate approach to an object to be measured. When a unit structure 50b oriented as shown in FIG. 9 is provided on the casing 60', the handle is provided as indicated by 60b.

Figure 10:
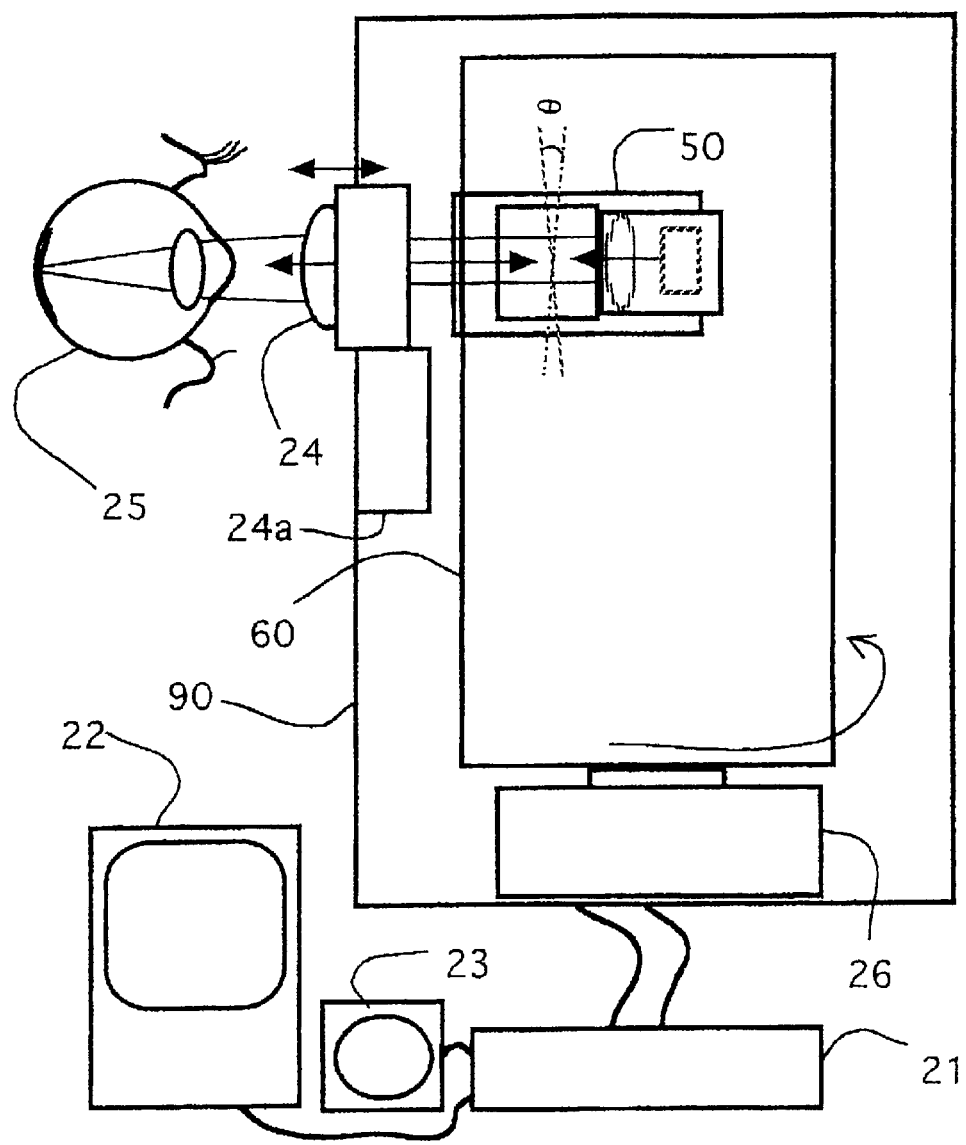
FIG. 10 is a view showing an embodiment in which the apparatus of the present invention is applied to an ophthalmic examination apparatus.

Next, FIG. 10 shows an embodiment in which the present apparatus is applied to an ophthalmic examination apparatus.

As shown in FIG. 10, the objective lens 10 shown in FIG. 5 is replaced with an objective lens 24 for funduscopy; a mechanism 24a for moving the lens 24 back and forth is provided; and an enclosure casing 60" is mounted on a rotary table 26. The irradiation position at the eyeground can be changed freely by appropriately controlling the rotary table 26 and the turning mechanism 51 shown in FIG. 7. The turning mechanism 51 is provided to constitute a tomographic image observation head 90 for ophthalmic use.

Figure 11:
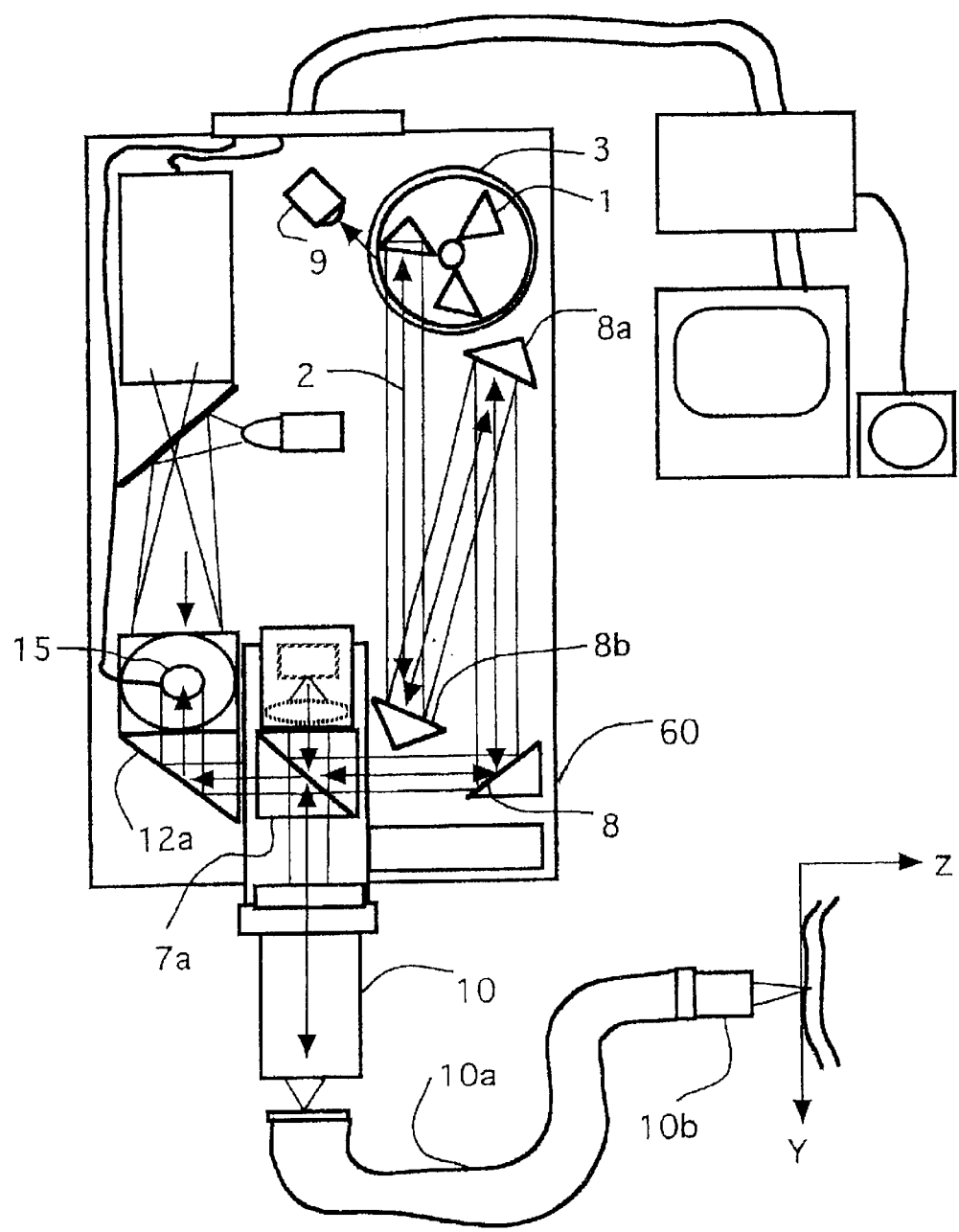
FIG. 11 is a view showing an embodiment of an optical interference tomographic image observing apparatus according to the present invention equipped with an optical bundle fiber.

Next, FIG. 11 is a view showing an embodiment of an optical interference tomographic image observing apparatus equipped with an optical bundle fiber, which is used as a probe for forming an optical path to an object to be measured.

The optical path of FIG. 7 which extends from the objective lens 10 to an object to be measured is replaced with an optical bundle fiber 10a as shown in FIG. 11. The optical bundle fiber 10a guides irradiation light emitted from the objective lens 10. For example, a GRIN lens (distributed index fiber-type lens) 10b is attached to the tip end of the fiber in order to radiate light onto the object. Reflection light from a deep portion of the object is collected by the lens and is caused to reach the photo detector 15, whereby a tomographic image is observed in the same manner as in the case of FIG. 7. In this case, the length of the optical path for reference light must be increased by the length of the fiber. Therefore, as shown in FIG. 11, a plurality of reflection mirrors 8a and 8b, etc. are used in order to turn the path up and down such that the path attains a desired length. Needless to say, a similar optical fiber may be disposed on the optical path for reference light. Moreover, it is apparent that the same observation is possible even when a distributed index fiber capable of transmitting images is used instead of the optical bundle fiber 10a (a bundle of fibers).

The present embodiment enables provision of endoscopes, microscopes, fiber catheters, and remote measurement in processes for fabricating various materials.

Figure 12:
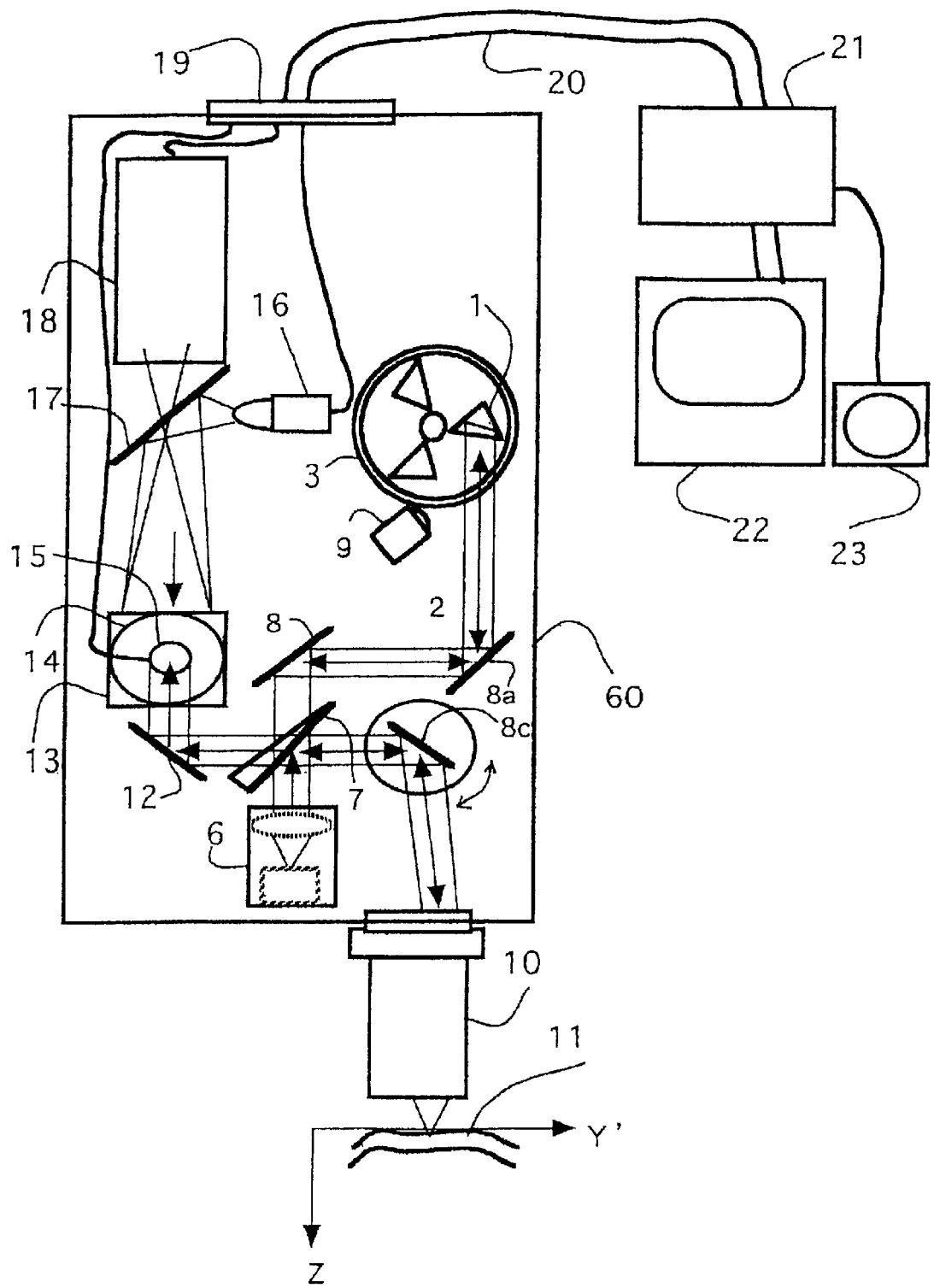
FIG. 12 is a view showing an embodiment of an optical interference tomographic image observing apparatus according to the present invention equipped with a galvanomirror scanning mechanism.

FIG. 12 shows an embodiment of an optical interference tomographic image observing apparatus equipped with a galvano-mirror scanning mechanism.

As shown in FIG. 12, a galvano-mirror 8c is provided in a path for object irradiation light in order to change the traveling direction of light radiated onto an object to be measured, to thereby sweep the irradiation point along the Y' axis in FIG. 12, whereby a desired tomographic image is obtained.

Figure 13:
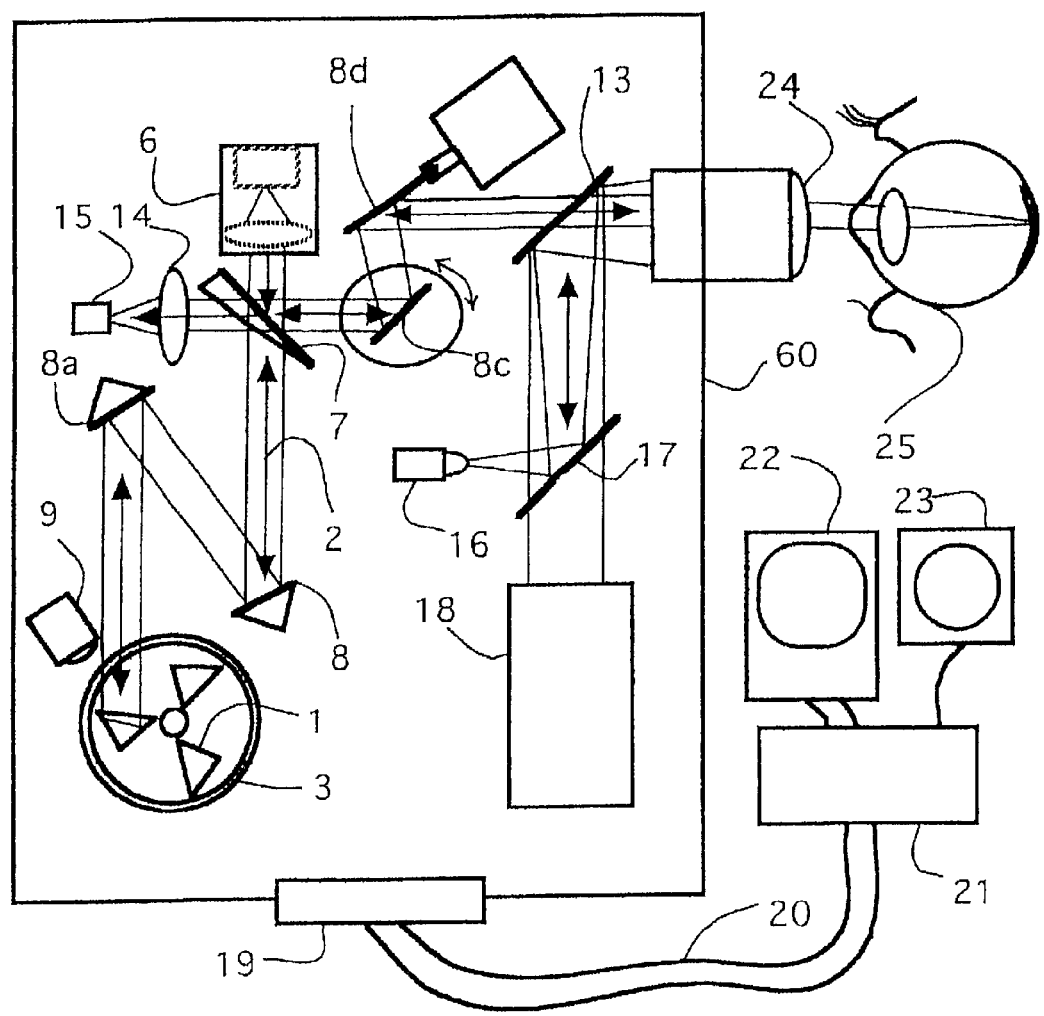
FIG. 13 is a view showing an embodiment of an optical interference tomographic image observing apparatus according to the present invention equipped with a two-axis galvano-mirror scanning mechanism.

FIG. 13 shows an embodiment in which another galvano-mirror 8d is disposed in order to enable scanning along the X-axis direction, to thereby constitute an apparatus for examination of the eyeball.

As shown in FIG. 13, by virtue of scanning along two directions, radiation light can be swept freely. The simplified compact apparatus which utilizes the features of the embodiment shown in FIG. 5 can be used with ease at medical sites.

Although wiring is partially omitted in FIGS. 12 and 13, apparently, a drive power source and wiring therefor are necessary.

Even when any of the structures of the embodiments is employed, there can be realized an optical interference tomographic image observing apparatus in which an object to be measured includes a dynamic scattering potential portion and generates object reflection light having a Doppler shift frequency, characterized by comprising a computer which passes a Doppler shift beat component output from the photo detector for detecting the mixture inference light through an electric filter and detects the Doppler shift beat component in order to synthesize a plurality of spatial pixel component signals, to thereby extract information regarding the amplitude of light scattered from the dynamic scattering potential portion; calculates and displays, on the basis of the frequency of the Doppler shift beat component, the moving speed and direction of the dynamic scattering potential portion for each three-dimensional pixels of a depth reflection image and a vertical cross-sectional image; thereby enabling visualization of a dynamic structure, such as blood flow distribution at a deep portion of a living body.

As described above, the present invention has the following features.

(1) There is provided a rotary prism which includes a Littrow reflector prism having a 90-degree vertex and disposed at a circumferential portion of a rotary body in such a manner that a surface facing the vertex extends substantially perpendicular to a tangential line of the circumference. The prism has a characteristics such that when a light beam impinges the surface, the light beam is reflected in a direction parallel to the incidence direction. Through utilization of the characteristics, the reflection point can be scanned in a predetermined direction as the rotary body rotates. A delay reflection light beam is periodically generated when the rotary body rotates in the travel direction of the light beam and a progressive reflection light beam is periodically generated when the rotary body rotates in the opposite direction. A means for splitting a light beam from a low-coherence light source into two light beams is provided. One of the light beams, serving as reference light, is delayed or advanced by means of rotary scanning of the reflection point in order to obtain a reflection light beam having a Doppler shift frequency. The other light beam is converged to an object to be observed which has a multilayer structure in terms of refraction index distribution. An objective lens is provided in order to capture object reflection light from a scattering potential portion at a deep portion of the multilayer object. A photo detector for performing heterodyne detection is provided in order to obtain a beat signal of the shift frequency, which is generated on the basis of the low coherence, characterized in that a maximum interference signal can be obtained only when the reference light and the object reflection light merge together after passage through respective optical paths having the same optical path length as measured from the split point. A means for calculating, in the form of coordinates, the scanned reflection point of the delay or progressive reflection light beam is provided. Further, a signal control processing system, a computer, and a display are provided in order to measure and display a reflection tomographic image, while using, as image data, the coordinates and an amplitude of the beat signal representing reflection light from the scattering potential at the deep portion of the object to be measured. The means for calculating, in the form of coordinates, the scanned reflection point of reflection light beam includes a photo detector for capturing deflection angle reflection light from the rotary prism, wherein the photo detector generates a timing pulse upon detection of the deflection angle reflection light before generation of the reflection light beam; and the scanned reflection point is calculated from the rotation frequency, rotation circumferential length, and rotation angle of the rotary prism, and is used as a coordinate of the scattering potential. Thus, an optical reflection tomographic image can be observed.

Moreover, the travel direction of the light beam emitted from the low-coherence light source is referred to as a Z axis; a semi-transparent reflection mirror is provided as the means for splitting the light beam into two beams; the objective lens is disposed in a direction toward which a light beam passing through the semi-transparent reflection mirror travels, the light beam serving as object irradiation light; a direction along which a reflection light beam from the semi-transparent reflection mirror serving as reference light travels is referred to as a Y axis; the light source, the semi-transparent reflection mirror, and the objective lens are integrated into a unit structure; and a mechanism for rotating the unit structure about the Y axis is provided in order to rotate the unit structure to thereby sweep the irradiation point on the object to be measured along the X-axis direction, whereby observation of a two-dimensional tomographic image on an X-Z plane is enabled. The respective means described in claim 2 are accommodated within a casing; a dielectric multilayer film reflection mirror which reflects only the wavelength band of the low-coherence light source is disposed before the photo detector in order to reflect and guide the mixed-wave interference wave to the photo detector; a light source whose wavelength band differs from that of the low-coherence light source is provided; a second half mirror is provided in order to reflect light emitted from the second light source and cause the light to pass through the dielectric multilayer film reflection mirror, the half mirror, and the objective lens in order to radiate the object to be measured, reflection light from the surface of the object traveling back along the above-described optical path, and passing through the second half mirror; a CCD camera is provided in the same casing in order to capture the image of the surface having magnified by the objective lens; and a display is disposed outside the casing in order to enable previous observation of a measurement position on the object. The casing described in claim 5 is equipped with a grip handle which has a switch for starting acquisition of measurement data of the tomographic image after positioning of the measurement point through observation of the measurement point. The optical interference tomographic image observing apparatus further comprises a rotation mechanism which rotates about the X axis and which receives the casing on which the unit structure is disposed at an angle of 90 degrees, whereby, in addition to the observation of a two-dimensional tomographic image on an X-Z plane, scanning along the Y-axis direction is effected by the rotation mechanism in order to enable observation of a three-dimensional tomographic image. The objective lens is replaced with an objective lens for funduscopy; the rotation mechanism described in claim 7 is provided; and thus a galvano-mirror scanning apparatus for ophthalmic measurement is provided. In the above-described apparatus, the optical path for reference light is turned up and down by use of a group of reflection mirror by a group of reflection mirrors in order to increase the length of the optical path;

and an optical fiber having a length corresponding to the increased length is disposed in the optical path extending between the half mirror for splitting and the object, whereby remote measurement is enabled. Alternatively, a fiber bundle or distributed index optical fiber, which can transmit images and has a length corresponding to the increased length is disposed in the optical path extending between the half mirror for splitting and the object, whereby remote measurement is enabled.

In order to increase operation speed, the optical interference tomographic image observing apparatus is provided with a computer display which detects conditions of a deep portion of an object to be measured over a desired area; and which records and stores a reproduction signal of each pixel, performs signal processing therefor, and displays the processed signal as a multidimensional deep-portion tomographic image.

The respective structures of the above-described embodiments may be modified without departing from the spirit of the present invention, and such modifications fall within the scope of the present invention.

The present invention is not limited to the above-described embodiments. Numerous modifications and variations of the present invention are possible in light of the spirit of the present invention, and they are not excluded from the scope of the present invention.

As have been described in detail, the present invention achieves the following effects.

(A) There are provided a method and a specific apparatus which utilizes a rotating Littrow reflector prism which can reflect a light beam in order to produce a delay reflection light beam or a progressive reflection light beam which travels toward the incoming direction of the light beam, even when the reflection point moves along a circumference of a rotary body upon rotation thereof or a surface of the prism facing the vertex thereof inclines. The method and the apparatus utilize the features of the prism such that the prism reflects a light beam toward the direction from which the light beam comes, and even when the incoming light beam inclines with respect to the surface facing the 90-degree vertex, the prism accurately reflects a light beam toward the incoming direction. Moreover, a reliable, high-speed-scanning reflection mirror can be realized by attaching prisms on a small, high-speed motor; and such a reflection mirror opens to the road to a compact, simplified, transportable apparatus which can be used practically for optical interference tomographic image observation.

(B) Moreover, reflection signals having a wide dynamic range and a high SN ratio can be extracted through high-speed scanning in order to detect a static or dynamic structure of a deep portion of, for example, a living body and to produce a multidimensional image. Thus, morphological information, medical information such as blood flow distribution, and structural information of various materials such as semiconductor materials, etc. can be observed in a non-invasive or non-destructive manner at high spatial resolution of a microscopic level. In addition, a novel, transportable, compact optical interference tomographic image observing apparatus can be provided. Moreover, the present invention is expected to create a new industry for practical apparatuses which can be used for various non-destructive material inspections and various non-invasive inspections for living bodies in relation to dermatology, cosmetic dermatology, and dentistry.

INDUSTRIAL APPLICABILITY

The optical interference tomographic image observing apparatus according to the present invention can detect a static or dynamic structure of a deep portion of, for example, a living body and to produce a multidimensional image. Thus, morphological information, medical information such as blood flow distribution, and structural information of various materials such as semiconductor materials, etc. can be observed in a non-invasive or non-destructive manner at high spatial resolution of a microscopic level. In particular, the optical interference tomographic image observing apparatus according to the present invention is suitable for various non-destructive material inspections and various non-invasive inspections for living bodies in relation to dermatology, cosmetic dermatology, and dentistry.

What is claimed is:

1. An optical interference tomographic image observing apparatus, characterized by comprising a rotary prism apparatus which includes a Littrow reflector prism having a 90-degree vertex and disposed near a circumference of a rotary body in such a manner that a surface facing the vertex extends substantially perpendicular to a tangential line of the circumference, the prism having a characteristics such that when a light beam impinges the surface, the light beam is reflected in a direction parallel to the incidence direction, wherein through utilization of the characteristics, the reflection point can be scanned in a predetermined direction as the rotary body rotates; and a delay reflection light beam is periodically generated when the rotary body rotates in the travel direction of the light beam and a progressive reflection light beam is periodically generated when the rotary body rotates in the opposite direction, wherein the optical interference tomographic image observing apparatus further comprises: means for splitting a light beam from a low-coherence light source into two light beams, one of the light beams, serving as reference light, being delayed or advanced by means of rotary scanning of the reflection point in order to obtain a reflection light beam having a Doppler shift frequency, and the other light beam being converged to an object to be measured which has a multilayer structure in terms of refraction index distribution; an objective lens for capturing object reflection light from a scattering potential portion at a deep portion of the multilayer object; a photo detector for performing heterodyne detection for obtaining a beat signal of the shift frequency, which is generated on the basis of the low coherence, characterized in that a maximum interference signal can be obtained only when the reference light and the object reflection light merge together after passage through respective optical paths having the same optical path length as measured from the split point; means for calculating, in the form of coordinates, the scanned reflection point of the delay or progressive reflection light beam; and a signal control processing system, a computer, and a display which measure and display a reflection tomographic image, while using, as image data, the coordinates and an amplitude of the beat signal representing reflection light from the scattering potential at the deep portion of the object to be measured.

2. An optical interference tomographic image observing apparatus as described in claim 1, wherein the means for calculating, in the form of coordinates, the scanned reflection point of the reflection light beam includes a photo detector for capturing deflection angle reflection light from the rotary prism, wherein the photo detector generates a timing pulse upon detection of the deflection angle reflection light before generation of the reflection light beam; and the scanned reflection point is calculated from the rotation frequency, rotation circumferential length, and rotation angle of the rotary prism, and is used as a coordinate of the scattering potential.

3. An optical interference tomographic image observing apparatus as described in claim 1, wherein the travel direction of the light beam emitted from the low-coherence light source is referred to as a Z axis; a semi-transparent reflection mirror is provided as the means for splitting the light beam into two beams; the objective lens is disposed in a direction toward which a light beam passing through the semi-transparent reflection mirror travels, the light beam serving as object irradiation light; a direction along which a reflection light beam from the semi-transparent reflection mirror serving as reference light travels is referred to as a Y axis; the light source, the semi-transparent reflection mirror, and the objective lens are integrated into a unit structure; and a mechanism for rotating the unit structure about the Y axis is provided in order to rotate the unit structure to thereby sweep the irradiation point on the object to be measured along the X-axis direction, whereby observation of a two-dimensional tomographic image on an X-Z plane is enabled.

4. An optical interference tomographic image observing apparatus as described in claim 1, wherein the respective means are accommodated within a casing; a dielectric multilayer film reflection mirror which reflects only the wavelength band of the low-coherence light source is disposed before the photo detector in order to reflect and guide the mixed-wave interference wave to the photo detector; a light source whose wavelength band differs from that of the low-coherence light source is provided; a second half mirror is provided in order to reflect light emitted from the second light source and cause the light to pass through the dielectric multilayer film reflection mirror, the half mirror, and the objective lens in order to radiate the object to be measured, reflection light from the surface of the object traveling back along the above-described optical path, and passing through the second half mirror; a CCD camera is provided in the same casing in order to capture the image of the surface having magnified by the objective lens; and a display is disposed outside the casing in order to enable previous observation of a measurement position on the object.

5. An optical interference tomographic image observing apparatus as described in claim 4, wherein the casing is equipped with a grip handle which has a switch for starting acquisition of measurement data of the tomographic image after positioning of the measurement point through observation of the measurement point.

6. An optical interference tomographic image observing apparatus as described in claim 3, further comprising a rotation mechanism which rotates about the X axis and which receives the casing on which the unit structure is disposed at an angle of 90 degrees, whereby, in addition to the observation of a two-dimensional tomographic image on an X-Z plane, scanning along the Y-axis direction is effected by the rotation mechanism in order to enable observation of a three-dimensional tomographic image.

7. An optical interference tomographic image observing apparatus as described in claim 6, wherein the objective lens is replaced with an objective lens for funduscopy; and the object irradiation light is scanned by use of a galvano-mirror.

8. An optical interference tomographic image observing apparatus as described in any one of claims 1 to 6, wherein the optical path for reference light is turned up and down by a group of reflection mirrors in order to increase the length of the optical path; and an optical fiber having a length corresponding to the increased length is disposed in the optical path extending between the half mirror for splitting and the object, whereby remote measurement is enabled.

9. An optical interference tomographic image observing apparatus as described in any one of claims 1 to 6, wherein an optical fiber is disposed in the optical path for reference light in order to increase the length of the optical path; and an optical fiber capable of transmitting images and having a length corresponding to the increased length is disposed in the optical path extending between the half mirror for splitting and the object, whereby remote measurement is enabled.

* * * * *